US005686417A

United States Patent [19]

MacFadden et al.

[11] Patent Number: 5,686,417

[45] Date of Patent: Nov. 11, 1997

[54] PEPTIDE T AND RELATED PEPTIDES IN THE TREATMENT OF HTLV-1 MYELOPATHY AND MULTIPLE SCLEROSIS

[75] Inventors: Douglas K. MacFadden; Peter L. Carlen; Penelope Reed Doob, all of Toronto, Canada

[73] Assignee: Reed MacFadden, Ltd., Canada

[21] Appl. No.: 554,758

[22] Filed: Nov. 8, 1995

Related U.S. Application Data

[63] Continuation of Ser. No. 232,360, Apr. 22, 1994, abandoned, which is a continuation of Ser. No. 858,832, Mar. 27, 1992, abandoned.

[51] Int. Cl.[6] .................... A61K 38/08

[52] U.S. Cl. .................... 514/16; 514/15; 514/17; 530/328; 530/329

[58] Field of Search .................... 514/15, 16, 17; 530/328, 329

[56] References Cited

U.S. PATENT DOCUMENTS 4,737,487 4/1988 Watts et al. .
5,162,499 11/1992 Trampota et al. .

FOREIGN PATENT DOCUMENTS

89/12067 12/1989 WIPO .

OTHER PUBLICATIONS

*Proc. Natl. Acad. Sci. USA*, vol. 83, Dec. 1986, Neurobiology, pp. 9254–9258, Pert, Candace B. et al., "Octapeptides deduced from the neuropeptide receptor-like pattern of antigen T4 in brain potently inhibit human immunodeficiency virus receptor binding and T-cell infectivity,".

*Clinical Neuropharmacology*, vol. 9, Suppl. 4, 1986, Raven Press, New York, pp. 482–484, Pert, C.B. and Ruff, M.R., "Peptide T[4–8]: A Pentateptide Sequence in the Aids Virus Envelope Which Blocks Infectivity is Essentially Conserved Across Nine Isolates.".

*Brain Research Bulletin*, vol. 19, pp. 629–633. Pergamon Journals Ltd., 1987, Barrera, Carlos M., et al., "D-[$Ala^1$]-Peptide T-Amide is Transported from Blood to Brain by a Saturable System.".

*1987 Federation of European Biochemical Societies*, vol. 211, No. 1, 17–22, FEB 04365, Jan. 1987, Ruff, Michael R., et al., "CD4 receptor binding peptides that block HIV infectivity cause human monocyte chemotaxis.".

*Nature*, 335, 639–642, Oct. 13, 1988, Brenneman, Douglas E., et al., "Neuronal cell killing by the envelope protein of HIV and its prevention by vasoactive intestinal peptide.".

*Drug Development Research*, 15:361–369 (1988), Brenneman, Douglas E., et al., "Peptide T Sequences Prevent Neuronal Cell Death Produced by the Envelope Protein (gp120) of the Human Immunodeficiency Virus.".

*Annals New York Academy of Sciences*, Komisaruk et al.: Analgesia Produced by VIP, pp. 650–654, "Analgesia Produced by Vasoactive Intestinal Peptide Administered Directly to the Spinal Cord in Rats.".

*The Lancet*, No. 8656, vol. II for 1989, Boston, Mass. and London, Sat., Jul. 22, 1989, "Improvement in Aids Patients on Peptide T.".

*Acta Derm Venereol (Stockh)* 1989, Suppl. 146:117–121, Marcusson, Jan A., et al., "Peptide T and Psoriasis.".

Heseltine, Peter et al., *Phase I Study of Peptide T in AIDS*, Abstract 3105 from IV International Conference on AIDS, Stockholm Sweden, Jun. 1988.

Ruff, Michael R. et al., Pharmacokinetics of Peptide T in Patients with Acquired Immunodeficiency Syndrome (AIDS), *Prog. Neuro-Psychopharmacol & Biol. Psychia*, 15:791–801 (1991).

MacFadden, D.K. et al., Role of Peptide T in Palliation of HIV-1-Related Painful Peripheral Neuropathy, VIIth International Conference on AIDS, Florence, 1991 W.B. 2173.

Farber, E.M. et al., Peptide T Improves Psoriasis when Infused into Lesions in Nanogram Amounts, *J. of American Academy of Dermatology*, pp. 658–664 (1991).

Bridge, T.P. et al., Results of Extended Peptide T Administration in AIDS and ARC Patients, *Psychopharmacology Bulletin*, 27:237–245 (1991).

Bridge, Peter et al., Neuropsychologic Results of Control HIV-1 Trial of Peptide T, VIIth International Conference on AIDS, Abstract Th.B.90, Florence, 1991 W.B. 2173.

Marastoni, M. et al., Synthesis, Metabolic Stability and Chemotactic Activity of Peptide T and its Analogues, *Int. J. Peptide Protein Res.*, 35:81–88 (1990).

Zorn, N.E. et al., Vasoactive Intestinal Peptide and Peptide T Activate Protein Kinase C in Purified Rat Spenocyte Nucleo, *The Endoc. Society*, Abstract (1989). Abstract 1105, p. 299.

Marcusson et al.; Acta Derm Venereol 1989; Suppl 146:117–121 "Peptide T and Psoriasis".

Bridge et al.; The Lancet 8656, vol. II 1989, Sat. Jul. 22, 1989 "Improvement in AIDS Patients on Peptide T".

*Primary Examiner*—Paula K. Hutzell
*Assistant Examiner*—Benet Prickril
*Attorney, Agent, or Firm*—Bell Seltzer Park & Gibson

[57] ABSTRACT

A composition useful in treating Multiple Sclerosis and HTLV-1 myelopathy in humans comprises:

i) a peptide having as its active portion, an amino acid sequence of the formula:

-Thr-Thr-Asn-Tyr-Thr-; and ii) a pharmaceutically acceptable carrier for said peptide.

4 Claims, No Drawings

PEPTIDE T AND RELATED PEPTIDES IN THE TREATMENT OF HTLV-1 MYELOPATHY AND MULTIPLE SCLEROSIS

This is a continuation of application Ser. No. 08/232,360 filed on Apr. 22, 1994, now abandoned which is a continuation of Ser. No. 07/858,832 filed on Mar. 27, 1992 now abandoned.

FIELD OF THE INVENTION

This invention relates to compositions useful in and methods of treating HTLV-1 myelopathy and Multiple Sclerosis as well as processes for formulating such compositions.

BACKGROUND OF THE INVENTION

Both multiple sclerosis (MS) and HTLV-1 associated myelopathy (HAM) affect the central and peripheral nervous systems and both may be present as a myelopathy affecting both the spinal nerves and the spinal myelinated nerve fibres.

Multiple sclerosis (MS) is a chronic demyelinating disease of the central nervous system and is the commonest chronic neurological disease of young adults. The incidence of MS and its pattern of distribution have been unchanged for decades. The disease remains essentially untreatable.

MS has always been regarded as a disease of the temperate zones and has a prevalence in the northern United States, Canada and Europe of 1:1000. The disease has a gender predilection of 1.5:1 (female:male).

MS usually affects multiple areas of white matter in the central nervous system (CNS), most frequently, the periventricular white matter, brainstem, spinal cord and the optic nerves. The primary process destroys myelin sheaths and eventually kills oligodendrocytes creating the characteristic plaque of MS.

The early development of the plaque is characterized by the development of perivascular inflammation followed by the migration of lymphocytes, plasma cells and macrophages into the lesions. This is followed by astrocyte gliosis and the attempts of remyelination by oligodendrocytes. The plaque is surrounded by lymphocytes.

Although the etiology of MS is still unknown, the focus of research efforts that have led to plausible hypotheses have been those of immune dysregulation including autoimmunity and genetic predisposition, both of which may play a role in the actual development of disease.

Multiple immunological abnormalities are reproducibly found in patients in the acute stage of the disease. The synthesis of immunoglobulins, although normal in the periphery, is increased in the central nervous system and the antibodies produced have a characteristic handing pattern. The antigenic specificity of these antibodies is not known and it is unclear whether they have a role to play in the progression of disease.

Various stressors known to activate the immune system such as viral infection or surgery can also produce an exacerbation of disease. Other activators such as gamma interferon produce similar effects when administered. In addition, immunosuppressive therapy with corticosteroids for example, can produce modest remission or at least palliation for short periods of time although this therapy is controversial.

Lymphocyte reactivity against two neuronal antigens, myelin basic protein and proteolipid has been demonstrated. Although not proven, this activity would form the basis for an autoimmune response against neuronal tissue.

The discovery of the neurotropic capacity of HTLV-1 in patients from Martinique with tropical spastic paraparesis (TSP) and in Japan with chronic myelopathy, has demonstrated HTLV-1 as the common etiologic agent of these diseases. It has subsequently been shown that the neurologic manifestations of HTLV-1 infection are the same despite the varied geographic regions in which they are described.

The neurological signs of this chronic retroviral infection include involvement of the pyramidal tracts in a bilateral and symmetrical fashion predominately at the thoracic level in the spinal cord and manifested by a slowly progressive spastic paraparesis with spastic bladder and minimal sensory deficits.

The peripheral nervous system has been shown to be involved in patients from Colombia and in the Seychelles and slowing of nerve conduction velocities in the lower limbs has been demonstrated. Systemic manifestations of HTLV-1 in patients with HTLV-1 myelopathy have been described and include inflammatory involvement of the lungs, skin, eyes and striated muscle producing a myositis. In addition, the patients experience profound fatigue similar to MS.

There are at least four possible pathogenetic mechanisms whereby HTLV-I can involve the CNS to produce HAM. These may include a slow virus infection, a cell-mediated lesion or by a predominately humoral immune mediated mechanism and the development of an autoimmune phenomenon. The slowly progressive course supports the hypothesis of a slow virus infection. The finding of perivascular cuffing in post-mortem specimens as well as transiently favourable response to steroids supports the possibility of an immune reaction responsible for the development of HAM.

These diseases have many similarities and dissimilarities, both clinical and neurological. Both diseases are a form of demyelinating disease whereby the myelin sheath of the nervous system is destroyed by one of many mechanisms common to both diseases and also peculiar to either of the diseases. MS is a multi-faceted disease in that it can be both a central nervous system disease as well as a form of myelopathy. Conversely, HTLV-1-associated myelopathy is both a form of myelopathy and can occasionally demonstrate central nervous system effects. Furthermore, MS can affect the peripheral nervous system in ways that are common in HTLV-1. Myelopathy, am already mentioned in being a disorder of the spinal cord, can be caused by many potential causes and not just MS or HTLV-1 Associated Myelopathy. These include:

neurosyphillis,

B 12 or folate deficiency, sarcoidosis, transverse myelitis, arachnoiditis, cervical spondylitis, motor neuron disease, neurofibromatosis, spinal cord compression from tumour, disc or arthritis, lupus erythematosus of the spinal cord and viral encephalomyelitis.

We have discovered that a particular peptide having at least 5 amino acid residues is a very effective agent useful in the treatment of at least MS and HAM, and predictably may be useful in treating other myelopathies of the above list some of which have similar disease mechanisms.

SUMMARY OF THE INVENTION

According to an aspect of the invention, a composition useful in treating MS and HAM in humans comprises:

i) a peptide having as its active portion, an amino acid sequence of the formula:

-Thr-Thr-Asn-Tyr-Thr- (SEQ ID NO:1); and ii) a pharmaceutically acceptable carrier for said peptide.

According to another aspect of the invention, a method for medically treating MS and HAM in humans comprises the administration on a repeated basis of a composition comprising:

i) a biologically effective amount of a peptide having as its active portion, an amino acid sequence of the formula:

-Thr-Thr-Asn-Tyr-Thr- (SEQ ID NO:1) ; and ii) a pharmaceutically acceptable carrier for said peptide.

According to another aspect of the invention, a process for formulating a composition useful in treating MS and HAM in humans, said process comprises mixing:

i) a peptide having as its active portion, an amino acid sequence of the formula:

-Thr-Thr-Asn-Tyr-Thr- (SEQ ID NO:1); with ii) a pharmaceutically acceptable carrier for said peptide,

DETAILED DESCRIPTIONS OF THE PREFERRED EMBODIMENTS

The active agent useful in accordance with this invention comprises:

i) a peptide having as its active portion, an amino acid sequence of the formula:

-Thr-Thr-Asn-Tyr-Thr- (SEQ ID NO:1)

These short peptides were first disclosed by Pert et al., EPO application 0 249 394 published Dec. 16, 1987.

It is appreciated that the peptide having the core sequence of Thr-Thr-Asn-Tyr-Thr- may have at both ends additional amino acid residues, some of which are by the formula:

X-Ser-Thr-Thr-Thr-Asn-Tyr-Y (SEQ ID NO:1) (I)

wherein X is an amino acid terminal residue selected from the group consisting of Ala and D-Ala and Y is a carboxy terminal residue selected from the group consisting of Thr and Thr-amide.

A particular preferred peptide of the group of peptides has the aforementioned core sequence of the -Thr-Thr-Asn-Tyr-Thr- (SEQ ID NO:1). These peptides of the above formula (I), and in particular a variant Peptide T of the formula -Ser-Thr-Thr-Thr-Asn-Tyr- (SEQ ID NO:1), were found to be very useful in inhibiting binding of the human immunodeficiency virus (HIV) to human cells by blocking receptor sites on the cell surfaces. The term Peptide T is used throughout the specification to reference peptides of formula (I) which all include the core peptide sequence. It is therefore intended that Peptide T encompass all of the compounds of formula (I) where it is understood that all such compounds are variants of the normally understood octapeptide T of the particular formula D-Ala-Ser-Thr-Thr-Thr-Asn-Tyr-Thr- (SEQ ID NO:1). Peptide T, in addition to preventing infectivity as discussed also may induce antibody production against the envelope protein of the HIV virus. It is thought that these peptides could therefore be used as vaccines to prevent development of Acquired Immune Disease Syndrome (AIDS). Monoclonal antibodies to these peptides would also be useful as diagnostic agents to identify HIV since the original identification of the short peptides by Pert et al supra. In order to provide a guideline for the adminstration of and insight into the use of the peptides and the treatment of MS, HAM and other forms of myelopathy and the formulation of the compositions, the following is offered as a guide based on the extensive work already conducted in the use of peptide T for treating HIV infections.

Peptide T is an octapeptide homologous to a region of gp120, an HIV envelope glycoprotein, and to vasoactive intestinal peptide (VIP). It was originally developed by Pert et al supra, to block the binding of gp120 to CD4 and prevent the binding of the virus (HIV) thereby blocking its internalization into the cell and subsequent replication. CD4 receptors which will facilitate viral entry into cells have been demonstrated on lymphocytes, macrophages, neurons and numerous other cells. Binding of HIV to the CD4 receptor has been demonstrated to effect viral entry. Binding of free (non-viral related) gp120 of the HIV envelope has resulted in neurotoxicity both in in vitro and in vivo studies.

The efficacy of Peptide T in reversing signs of HIV-induced dementia has been demonstrated in both the Peptide T Phase I clinical trial at the University of Southern California in Los Angeles and in the Phase II clinical trial at the Penway Clinic in Boston. Both studiesa have demonstrated improvement in the HIV-induced neurocognitive impairment in patients with AIDS.

To date, the Peptide T/gp120/VIP homology has been used to explain at least two possible mechanisms of action of Peptide T. Firstly, that it competitively binds to CD4 (the known receptor for HIV) on human cell surfaces and competes with both HIV and gp120 for binding sites.

The binding of Peptide T and its analogues of formula (I), to CD4 could produce a blocking effect to prevent the binding of any other molecule capable of binding to that receptor; alternatively, or in addition, the binding of Peptide T to CD4 could induce a reaction similar to that caused by the endogenous ligand.

CD4 is the differentiation antigen that defines the T lymphocyte subgroup of helper/inducer cells, but it is also present on a wide variety of cells including neurons, activated macrophages and B cells. CD4 is the predominant receptor for HIV and was originally thought to be necessary for cellular infection. Using the monoclonal antibody OKT4, Pert et el. (1 & 2) demonstrated the presence of this antigen throughout the human CNS and showed that it is present in highest concentration in the dentate gyrus, hippocampus, amygdala and deep cortex. This distribution was found to be similar in other higher mammals. Peptide T and similar analogues were found to inhibit the binding of radiolabelled gp120 to rat hippocampal membranes and to do so in 0.1 nM concentrations.

Using Peptide T and the same analogues, Pert et el. (1 & 2) were able to demonstrate a reduction in the detectable levels of HIV reverse transcriptase when these peptides were present in an assay of HIV infectivity. A ninefold reduction of reverse transcriptase took place at 100 nM concentrations of Peptide T.

Since gp120 is not identical in all isolated strains of HIV, a comparison was made with nine different HIV isolates Pert et el. (2). Significant homology was found between the isolates examined and Peptide T when comparison was made with the core pentapeptide, peptide T(4-8). This comparison has now been extended to over twenty isolates.

The inhibition of gp120 and HIV binding to CD4, as well as the demonstration of reduced infectivity of HIV in the presence of Peptide T and its analogues, provides one possible mechanism of action to explain the clinical effects of Peptide T. In this regard, Peptide T in sufficient concentration may prevent new cellular infection with HIV. Initial research in this area was focused on the CNS for two reasons: a high concentration of CD4 molecules was found on neurons and one of the major effects of HIV infection is the development of neurocognitive dysfunction. These facts are particularly important given that Peptide T is transported from the blood to the brain by an active, saturable transport system, while its exit is by diffusion only, [Barrera et al. (3)].

Although it is well accepted that HIV can infect not only lymphocytes but also neurons, it is difficult to ascribe the neurologic dysfunction seen in HIV patients to active CNS HIV infection, since only a small number of neurons are actively infected. It has been suggested that the neural deficits seen in HIV infection may occur not only as a result of infection but also as a result of a viral "toxin," such as gp120. Brenneman et el. *Nature*, 1988 (5) found that purified gp120 from two isolates as well a recombinant gp120 produced significant neuronal cell death in cultures of mouse fetal hippocampal neurons. Neurotoxicity could be reduced by pretreatment with antibody to CD4 and was completely eliminated by VIP. Since mouse neurons are not infected with HIV, it is evident that neurotoxicity is gp120-induced and is not a result of viral entry or replication.

VIP (8-12: TDNYT) and the core peptide (4-8: TTNYT) share the homologous sequence that binds CD4, and that is also found in isolates of the much larger gp120. Peptide T, when used in the same mouse hippocampal neuronal culture system, completely, antagonized the gp120-induced neurotoxicity, Brenneman, *Drug Development Research* (6), In addition, CSF from a patient with AIDS dementia produced substantial neurotoxicity in this system (44–49% killing at 1:100,000 dilution). This effect was inhibited by Peptide T, Buzy et el., *Amer J Med*, (8). Normally gp120 is produced in vast excess of amounts required for viral replication; this excess gp120 may exert a neurotoxic effect far out of proportion to the number of neurons actively infected with HIV.

Peptide T may also act as an agonist in addition to or even without its protective effects against viral infection and neurotoxicity. In addition, direct agonist activity has been demonstrated in two ways. Ruff et el. *FEBS Letters*, (4) showed that Peptide T and two analogues were potent agonists of human monocyte chemotaxis. Their rank order potency as chemotactic agents corresponded to their relative ability to inhibit both gp120 binding and HIV T cell infectivity.

As a further demonstration of the agonist activity of Peptide T, both Peptide T and VIP exert their cellular effects via the regulation of protein kinase C. Zorn et el., (11). Agonist activity of Peptide T is thus implied by the production of a transmembrane signal that can influence the regulation of protein kinase C.

Further evidence of Peptide T's potential VIP-like agonist activity is provided by results from experimental testing of the hypothesis of Komisaruk et al. (7) that VIP released from pelvic nerve terminals into the spinal cord can produce analgesia. Knowing that naloxone-independent analgesia produced by administration of VIP to the periaqueductal grey matter in rats had been shown they attempted VIP administration directly to rat spinal cord and measured the pain threshold to distal noxious stimuli to test the hypothesis. Spinal administration of VIP produced analgesia as measured by the fail-flick latency test and the tail-shock induced vocalization test by action on both opiate and non-opiate modulated pain pathways, Komisaruk et al., 1988 (7).

The existence of clinical benefits from the administration of Peptide T to humans has been suggested in all studies to date: in HIV disease, by the pilot Swedish data, the USC Phase I and Fenway/CRI studies, and the Toronto Western Hospital compassionate administration to 41 patients; in psoriasis and other medical conditions, in case reports from Sweden (Marcusson, Lazega, et al., 1989-9, end Marcusson and Wetterberg, 1989-10) and in 8 patients with psoriasis or other medical conditions in Toronto.

Neurocognitive improvement found in HIV positive patients and improvement in constitutional symptoms in both HIV positive and HIV negative patients may well depend primarily on Peptide T's VIP-like neurotropic and agonist effects.

Not wishing to be bound by any particular theory, with respect to the use of these peptides with treatment of MS and HAM, and in view of the above guidelines and discussions in relation to the use of various peptides of formula (I) and their analogues in the treatment of HIV, it is hypothesized that there are numerous similarities of disease expression and potential similarities of disease etiology. Peptide T appears to act as an agonist and as a blocker of CD4-mediated immune function rather than as an antiviral drug. In our investigations, patients with non-HIV disease such as psoriasis, multiple sclerosis, HTLV-1 associated myelopathy and chronic fatigue syndrome have all been treated with Peptide T.

Now that we have discovered the effectiveness of these peptides of formula (I), we suggest the following as hypothesis as to why the compounds do work:

1) both HAM and MS are chronic CNS diseases as is HIV disease 2) both diseases have possible viral etiologies; it is now generally accepted that HAM is caused by the retrovirus, HTLV-1, a virus in the same family as HIV; MS has also been suggested as a manifestation of HTLV-1 infection and the chronic fatigue syndrome has recently been linked to a number of possible viral infections both of DNA and retroviral etiologies, 3) the two diseases share a number of common symptoms, for example, fatigue, lack of balance and signs of autoimmune phenomena; it is worth while noting that HTLV-1 disease exhibits numerous signs of autoimmunity such that it maybe expected that some retroviral diseases have a concomitant expression in autoimmune phenomena. One common theme among these diseases may be peripheral neuropathy which is based on the process of demyelination.

4) the basis appears to be the common denominator of both demyelination whether it be in the central or peripheral nervous system and the common autoimmune manifestations in HAM, MS and HIV disease.

In accordance with various embodiments of this invention and in view of the above guidelines gained from the use of peptides of formula (I) in the treatment of HIV, similar doses of peptide T and its analogues can be administered to humans for purposes of treating MS, HAM and other forms of myelopathy. The peptides, according to this invention as used in the compositions, may be formulated for injection or other routes of administration which include intranasal, oral, buccal, topical, rectal and various injection approaches. Compositions as adapted to these various routes of administration will be in solution, suspension or emulsion combined with the use of various formulating agents which include suspending agents, stabilizing agents and dispensing agents. It is understood that in the administration of the compounds they may be in lyophilized form which are then put into solution for the purpose of administrated. It is understood that the compositions of this invention may contain from 0.001 to 99.9% of the active peptide. For administration by injection or infusion of the composition the daily dosage, as employed for treatment of adults of approximately 70 kg of body weight, will range from 0.2 mg to 20 mg of active material which may be administered in the form of 1 to 4 doses over each day. Such dosage ranges depending upon the route of administration and the condition of the patient.

The selected peptide of formula (I) for use in this composition may be synthesized in accordance with any normal manufacturing techniques. For example, peptide synthesis may be routinely used to produce such short peptides by either solid phase or liquid phase methods. The solid phase method may be the usual Merrifield technique. It is appreciated however that the peptide could be synthesized using recombinant techniques and optionally treated with enzymes for providing peptide length. In accordance with a preferred aspect of this invention, the preferred peptide T is made by peptide synthesis and is readily obtained from Carlbiotech S/A Copenhagen, Denmark. The peptide is usually formulated and packaged in a sterile manner in 5% dextrose solution in multi-dose vials. It is appreciated that the peptide may be packaged in other carriers which may include saline. Preferably the concentration of peptide in each does is in the range of 8.5 mg/ml for subcutaneous injection.

In order to demonstrate the significant effects that the peptides of formula (I) have on MS and HAM, the following examples are provided which are in no way intended to be limiting with respect of the scope of the accompanying claims. The peptide used in each of the following examples is a variant Peptide T of formula (I) having the sequence D-Ala-Ser-Thr-Thr-Thr-Asn-Tyr-Thr- Amide (SEQ ID NO:1).

EXAMPLES

Example 1

HTLV-1 Myelopathy

A 45 year old female was diagnosed as HTLV-1 seropositive after experiencing dysesthesia of the feet, pain in the feet and legs, weakness of the legs and urinary frequency. Her neurological examination confirmed increased reflexes, spasticity of the lower limbs and pyramidal weakness of the legs. The diagnosis was confirmed by somatosensory and auditory evoked potentials and HTLV-1 seropositivity. Therapy consisting of 10 milligrams of Peptide T was given subcutaneously each morning. In two months time, the patient reported feeling improved. She could lift both feet off the ground instead of dragging them and could walk without a cane. She could stand without support and experienced decreased burning in her feet and knees, could climb stairs for the first time in 2 years, and had decreased urinary frequency.

After another 2 months of therapy, the patient was still experiencing decreased symptoms and improved walking. Her neurological examination remained unchanged.

Having run out of Peptide T during a holiday, the patient was without therapy for 5 days and noted progressive fatigue and became bed-bound. Within two weeks of stopping the Peptide T treatment, all of her symptoms had recurred and on restarting Peptide T, her symptoms again resolved. At various times she stopped therapy and her symptoms worsened but when restarted, she improved.

Example 2

Multiple Sclerosis

A 40 year old female was diagnosed as having MS after presenting with weakness, loss of balance, double vision, and paraesthesia in her right arm at age 23. She was treated with prednisone and later with physiotherapy. She remained unable to walk without a cane or a walker, was depressed, showed horizontal nystagmus, and weakness of hip flexors bilaterally, weakness of knee flexors and of dorsilflexors of the feet. Tone was increased in both lower limbs and she had bilateral ankle clonus. Deep tendon reflexes were 2+ in the arms, 3+ in both knees and ankles and the planter responses were extensor. She was treated with Lioresal (Baclofen) with some improvement; however, she experienced progressive worsening until she became wheelchair dependent and complained of weakness, spasticity, clonus, urinary incontinence and recurrent urinary tract infections. When she was evaluated her MRI scan of the brain showed findings consistent with multiple sclerosis.

She was started on 10 milligram subcutaneous injections of Peptide T daily. After 1½ weeks, her symptoms had improved. She was assessed again after about 5 weeks and reported functional improvement. After 6 months she was showing maintained improvement in her symptoms. Her frequency of nocturia was reduced, fine motor control improved, stuttering decreased, her legs were less spastic and she could stand with minimal support. She showed marked symptomatic improvement in intellectual and motor functioning within a few weeks after starting treatment with Peptide T, such improvement being sustained over a 6 month period. Worsening of symptoms occurred when the patient stopped Peptide T for 3 weeks, but improves when she restarted the drug.

Example 3

Multiple Sclerosis

A 28 year old female was diagnosed with optic neuritis secondary to multiple sclerosis after presenting with numbness, impaired motor function, and blurred vision (20/300 bilaterally). Her somatic neurological examination was within normal limits. Minor episodes of numbness and impaired speech, balance and co-ordination had occurred over 6 months, as well as headache and loss of vision.

Peptide T therapy was started. Six (6) days later a reassessment showed remarkably improved visual acuity (21/30 bilaterally). The patient noted functional improvement over the next week. A prior episode of optic neuritis took six months to recover (compatible with the natural history of MS) compared to this episode which recovered much more quickly than would be expected for an episode of MS-induced optic neuritis.

Example 4

Multiple Sclerosis

A 34 year old woman with her first multiple sclerosis episode had optic neuritis and complete blindness in the right eye for 2 weeks, numbness in her right leg and then both legs. Her symptoms worsened. She was give prednisone and experienced some improvement. She had worsening of her ataxia and blurred vision. She was given prednisone 80 milligrams per day. An MRI scan showed multiple high intensity signals periventricularly as well as in the brain stem, consistent with the diagnosis of MS. The patient complained of oscillopsia. The ataxia and some visual problems seemed to improve on steroids. Another MRI scan about 16 months later showed extensive periventricular white matter disease with involvement of the corpus collosum. Findings were typical of demyelination consistent with MS. At that time the patient showed resting oscillatory lateral beating nystagmus and lateral nystagmus with bilateral gaze, an ataxic gait, a slight impairment on her heel shin test but good finger nose testing. The tone was increased in her lower limbs and she had non-sustained ankle clonus bilaterally. Her knee jerk was increased on the right compared to the left. Plantar responses were both upgoing. She had decreased position, vibration, light touch and cold sensation in the feet compared to the hands.

About 2 months later the patient was started on Peptide T 10 milligrams subcutaneously daily. Within 1 to 2 weeks she reported subjective improvement. She experienced improved feelings in her fingers, fine movements of her hands and improved cognitive function. When she stopped Peptide T therapy she noticed an increased fatigue and ataxia. She obtained minimal symptomatic improvement from prednisone 150 mg daily. After restarting Peptide T, she noted a remarkable improvement of her fatigue, ataxia and fine motor function.

Example 5

Multiple Sclerosis

A 56 year old female with a history of dizziness, ataxia, episodes of vertigo, impairment of motor function and generalized weakness of the legs was treated with dilantin and admitted to hospital. Subsequent examination showed vertical nystagmus, some saccadic smooth pursuit and an impaired tandem gait. She was reassessed about 2 years later for episodes of dizziness, and complaints of leg spasms. Her physical examination showed decreased visual fields with a partial left lateral hemianopsia in the lateral field and a right constricted field. She showed impaired tandem gait, decreased right hip flexion and strength and decreased deep tendon reflexes in the right brachioradialis compared to the left and in the right knee compared to the left. Planter response was downgoing and she had upwards gaze vertical nystagmus as previously noted.

The patient was treated with Peptide T 10 milligrams subcutaneously daily and within 10 days reported increased energy and intellectual function, and improved vision. When Peptide T therapy was stopped, she regressed symptomatically to her pre-drug status. Her physical examination at that time showed no change from her examination before Peptide T therapy was begun.

Although preferred embodiments of the invention are described herein in detail, it will be understood by those skilled in the art that variations may be made thereto without departing from the spirit of the invention or the scope of the appended claims.

REFERENCES

Pert, C. B., Will, J. M., Ruff, M. R., Berman, R. M., Robey, W. G., Arthur, L. O., Ruscetti, F. W. and Farrar, W. L. Octapeptidies Deduced from the Neuropeptide Receptor-Like Pattern of Antigen T4 in Brain Potently Inhibit Human Immunodeficiency Virus Receptor Binding and T-Cell Infectivity. *Proc. Natl. Sci. U.S.A.* 83:9254–9258, 1986.

2. Pert, C. B. and Ruff, M. R. Peptide $T_{4-8}$: A Pentapeptide Sequence in the AIDS Virus Envelope which Blocks Infectivity is Essentially Conserved Across Nine Isolates. *Clin. Neuropharmacol.*, 9(4)S198, 1986.
3. Barrera, C. M., Kastin, A. J. and Banks, W. A. D-($Ala^1$)-Peptide T-Amide is Transported from Blood to Brain by a Saturable Systems. *Brain Res. Bull.* 19:629–633, 1987.
4. Ruff, M. R., Martin, M. B., Ginns, E. I., Farrar, W. L., Wahl, S. M. and Pert, C. B. CD4 Receptor Binding Peptides that Block HIV Infectivity Cause Human Monocyte Chemotaxis: Relationship to Vasoactive Intestinal Polypeptide. *FEBS Lett.* 211:17–22, 1987.
5. Brenneman, D. E., Westbrook, G. L., Fitzgerald, S. P., Ennist, D. L., Elkins, K. L., Ruff, M. R. and Pert, C. B. Neuronal Cell Killing by the Envelope Protein of HIV and its prevention by Vasointestinal peptide. *Nature.* 335:639–642, 1988.
6. Brenneman, D. E., Buzy, J. M., Ruff, M. R. and Pert, C. B. Peptide T Sequences Prevent Neuronal Cell Death Produced by the Envelope Protein (gp120) of the Human Immunodeficiency virus. *Drug Dev. Res.* 15:361–369, 1988.
7. Komisaruk, B. R., Banas, C., Heller, S. B., Whipple, B., Barbat, G. and Jordan, F. Analgesia Produced by Vasoactive Intestinal Peptide Administered Directly to the Spinal Cord in Rats. In *Vasoactive Intestinal Peptide and Related Peptides.* Ed. Said, S. I. and Mutt, V. *Annals of the NY Acad. Sci.* 527:650–654, 1988.
8. Buzy, T. P., Haseltine, P. N. R., Parker, E. S., Eaton, E., Ingraham, L. J., Gill, M., Ruff, M. R., Pert, C. B. and Goodwin, F. K. Improvements in AIDS Patients on Peptide T. *The Lancet,* July 22, pp. 226–227, 1989.
9. Marcusson, J. A., Lazega, D., Pert, C. B., Ruff, M. R., Sundquist, K. G. and Wetterberg, L. Peptide T and Psoriasis. *Acta. Derm. Venerol. (Stockh.)* Suppl. 146:117–121, 1989.
10. Marcusson, J. A., and Wetterberg, L. Peptide-T in the Treatment of Psoriasis and Psoriatic Arthritis; A Case Report. *Acta. Derm. Venereol. (Stockh.)* Suppl. 69:86–88, 1989.
11. Zorn, N. E., Buckley, A. R. and Russell, D. H. Vasoactive Intestinal Peptide and Peptide T Activate Protein Kinase C in Purified Rat Spenocyte Nuclei. *The Endoc. Society.* (Abstract), 1989.

We claim:

1. A method for alleviating neurological, cognitive or motor symptoms of myelopathy associated with multiple sclerosis or HTLV-1 in humans, comprising the parenteral administration on a daily basis of a composition comprising:

i) a peptide in an amount effective to alleviate neurological, cognitive or motor symptoms of myelopathy associated with multiple sclerosis or HTLV-1, said peptide having the formula:

D-Ala-Ser-Thr-Thr-Thr-Asn-Tyr-Thr-amide (SEQ ID NO:1);

ii) a pharmaceutically acceptable carrier for the parenteral administration of said peptide.

2. A method of claim 1 for alleviating symptoms of myelopathy associated with multiple sclerosis.

3. A method of claim 1 for alleviating symptoms of HTLV-1 associated myelopathy.

4. A method for alleviating neurological, cognitive or motor symptoms of myelopathy associated with multiple sclerosis or HTLV-1 in humans, comprising the intranasal administration on a daily basis of a composition comprising:

i) a peptide in an amount effective to alleviate neurological, cognitive or motor symptoms of myelopathy associated with multiple sclerosis or HTLV-1, said peptide having the formula:

D-Ala-Ser-Thr-Thr-Thr-Asn-Tyr-Thr-amide (SEQ ID NO:1);

ii) a pharmaceutically acceptable carrier for the intranasal administration of said peptide.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

-continued ( i ) SEQUENCE CHARACTERISTICS:
( A ) LENGTH: 8
( B ) TYPE: Amino Acid
( C ) STRANDEDNESS: Not Applicable
( D ) TOPOLOGY: Not Applicable ( i x ) FEATURE:
( D ) OTHER INFORMATION: The amino acid terminal residue selected from the group consisting of Ala and D-Ala and the carboxy terminal residue Xaa is selected from the group consisting of Thr and Thr-amide.

( x i ) SEQUENCE DESCRIPTION: SEQ ID NO: 1:

```
Xaa Ser Thr Thr Thr Asn Tyr Xaa
 1               5
```